United States Patent
Asada et al.

[11] Patent Number: 5,964,701
[45] Date of Patent: Oct. 12, 1999

[54] PATIENT MONITORING FINGER RING SENSOR

[75] Inventors: Haruhiko H. Asada, Concord; Boo-Ho Yang, Boston; Kai-Yeung Sunny Siu, Charlestown; Kuo Wei Chang, Lexington, all of Mass.

[73] Assignee: Massachusetts Institute of Technology, Cambridge, Mass.

[21] Appl. No.: 08/957,789

[22] Filed: Oct. 24, 1997

Related U.S. Application Data

[63] Continuation-in-part of application No. 08/954,889, Oct. 8, 1997
[60] Provisional application No. 60/029,253, Oct. 24, 1996.

[51] Int. Cl.⁶ .................................................. A61N 5/00
[52] U.S. Cl. .......................................... 600/300; 128/903
[58] Field of Search ........................... 128/903; 600/300, 600/301, 322, 483, 561, 549

[56] References Cited

U.S. PATENT DOCUMENTS

| | | | |
|---|---|---|---|
| 3,835,839 | 9/1974 | Brown | 128/2.05 F |
| 3,878,502 | 4/1975 | Rochelle | 340/5 R |
| 3,972,038 | 7/1976 | Fletcher et al. | 340/189 M |
| 3,972,320 | 8/1976 | Kalman | 128/2.1 |
| 4,063,410 | 12/1977 | Welling | 58/38 R |
| 4,396,906 | 8/1983 | Weaver | 340/347 DD |
| 4,535,324 | 8/1985 | Levental | 340/574 |
| 4,700,708 | 10/1987 | New, Jr. et al. | 128/633 |
| 4,799,062 | 1/1989 | Sanderford, Jr. et al. | 342/450 |
| 4,825,872 | 5/1989 | Tan et al. | 128/633 |
| 4,827,943 | 5/1989 | Bornn et al. | 128/668 |
| 4,924,450 | 5/1990 | Brashear et al. | 367/118 |
| 5,152,296 | 10/1992 | Simons | 600/483 |
| 5,285,784 | 2/1994 | Seeker | 128/633 |
| 5,297,548 | 3/1994 | Pologe | 600/322 |
| 5,511,546 | 4/1996 | Hon | 128/633 |
| 5,638,818 | 6/1997 | Diab et al. | 128/653.1 |
| 5,661,460 | 8/1997 | Sallen et al. | 340/573 |
| 5,694,939 | 12/1997 | Cowings | 128/905 |
| 5,738,102 | 4/1998 | Lemelson | 600/483 |
| 5,771,001 | 6/1998 | Cobb | 128/903 |

FOREIGN PATENT DOCUMENTS

| | | |
|---|---|---|
| 0467853 A1 | 1/1992 | European Pat. Off. . |
| 0706776 A1 | 4/1996 | European Pat. Off. . |
| 0724860 A1 | 8/1996 | European Pat. Off. . |
| 2655834 A1 | 6/1991 | France . |
| 3609913 A1 | 10/1987 | Germany . |
| WO 93/16636 | 9/1993 | WIPO . |

*Primary Examiner*—Robert L. Nasser
*Assistant Examiner*—Michael Astorino
*Attorney, Agent, or Firm*—Bromberg & Sunstein LLP

[57] ABSTRACT

A monitoring system for monitoring the health status of a patient and transmitting to a remote receiver a signal, based on measured physiological parameters. A sensor is incorporated in a finger ring or other article of apparel so as to monitor skin temperature, blood flow, blood constituent concentration, or pulse rate of the patient. The data are encoded for wireless transmission by mapping a numerical value associated with each datum to a pulse emitted after a delay of a specified duration following a fiducial time. Multiple ring bands and sensor elements may be employed for deriving three-dimensional dynamic characteristics of arteries and tissue of the finger.

16 Claims, 4 Drawing Sheets

PATIENT MONITORING FINGER RING SENSOR

The present application is a continuation-in-part of U.S. patent application Ser. No. 08/954,889, filed Oct. 8, 1997, and claims priority from U.S. provisional application number 60/029,253, filed Oct. 24, 1996, which is herein incorporated by reference.

FIELD OF THE INVENTION

This invention relates to a method and apparatus for monitoring the health status and location of a patient and sending a warning of abnormality to a medical professional.

BACKGROUND ART

The population of aged people living alone is expected to continue its recent upward trend. As people live longer and the social and economic circumstances continue to change, more aged people live alone having no supervision or limited attendance by caregivers, and aged spouses may be unable to properly care for each other. Such individuals suffer a high risk of accidents, and this is a major concern and even a fear for those aged people living alone.

Close monitoring is the key to avoiding or responding to such accidents or medical emergencies. While technologies are known for remotely monitoring certain physiological parameters, these tend to be cumbersome and a patient may easily forget to don the monitor if it is removed, for example, while taking a shower. Less cumbersome monitors require strategies for prolonging the life-time of the battery or other energy source which provides power for transmitting the monitored physiological parameters and which is necessarily limited by the space available for housing it. The limited power source must be used efficiently so that even a tiny battery may last for a reasonable period of time, on the order of a few months. Among many components involved in a remote monitoring device, a radio transmitter may consume over 40% of the total power, hence power saving in the radio transmitter will make a significant contribution to the extension of battery life. A power-saving wireless transmission protocol is thereby desirable for this and other power-sensitive applications.

The most power-consuming part of digital RF transmitters is often an oscillator circuit involving a CMOS power transistor, which consumes a significant amount of power only when the output is high, i.e. 1-bit. Therefore significant energy may be saved by minimizing the total duration of time the output is high.

SUMMARY

In accordance with a preferred embodiment of the present invention, a patient's health status is monitored by an article of apparel, such as a finger ring, equipped with miniaturized sensors and a wireless transmitter. The finger ring sensor may be worn by the patient at all times, hence the health status is monitored 24 hours a day. The sensors packed into the finger ring may include a thermocouple for measuring skin temperature, an electrical impedance plethysmograph, and one or more optical sensors for pulse count and measurements of blood constituent concenetration and blood flow. The sensor data are transmitted to a computer through a wireless communication link and the patient status is analyzed continually and remotely. Any trait of abnormal health status and possible accidents is detected by analyzing the sensor data. Both the physiological sensors and the position sensor are used to make an accurate decision as to whether a warning signal must be sent to a medical professional caring the patient. This monitoring system is particularly useful for caring for the elderly living alone and patients with minor impairments at potential risk by reason of living alone.

In further accordance with a preferred embodiment of the present invention, there is provided a monitoring system for monitoring the health status of a patient based on an article of apparel, to be worn by the patient, that has at least one sensor for providing a signal based on at least one of skin temperature, blood flow, blood constituent concentration, and pulse rate of the patient and a transmitter for converting the signal to a wave. The wave may be any form of wireless communication between the monitor and at least one receiver for receiving the wave. Additionally, the monitoring system has a controller for analyzing the wave and determining an abnormal health status.

In accordance with alternate embodiments of the present invention, the monitor may include a sensor that in a temperature sensor for monitoring skin temperature, and an optical sensor for measuring at least one of the blood flow, blood constituent concentration, and pulse rate of the patient.

In accordance with another aspect of the present invention, there is provided a method for encoding a datum, the method comprising the steps of associating a number with the datum, mapping the number to a specified duration of time, and representing the datum by a pulse emitted after a delay following a fiducial time wherein the delay equals the specified duration of time. A plurality of data may thus be communicated, in accordance with an embodiment of the invention, by associating a numerical value with each datum, mapping the numerical value to a specified duration of time, and transmitting a pulse after a delay following a periodic fiducial time, wherein the delay equals the specified duration of time. The step of transmitting may also include emitting an electrical or electromagnetic pulse after a delay following a periodic fiducial time, wherein the delay equals the specified duration of time.

In accordance with yet a further aspect of the present invention, in one of its embodiments, there is provided a method for monitoring the health status of a patient. The method has a first step of providing a monitor to be worn by the patient, where the monitor has at least one sensor for providing a measurement based on at least one of skin temperature, blood flow, blood constituent concentration, and pulse rate of the patient, and a transmitter for converting the signal to a wave. Further steps of the method are those of associating a numerical value with the measurement, mapping the numerical value to a specified duration of time, transmitting a pulse after a delay following a periodic fiducial time, wherein the delay equals the specified duration of time, receiving the pulse, and analyzing the delay between the periodic fiducial time and the received pulse wave to determine an abnormal health status.

DETAILED DESCRIPTION OF SPECIFIC EMBODIMENTS

Advantages of the present invention and its several improvements will be seen when the following detailed description is read along with the attached drawings. These drawings are intended to provide a better understanding of the present invention, but they are in no way intended to limit the scope of the invention.

A finger ring is nonintrusive and can be worn at all times. Even when taking a shower, people keep wearing rings. Therefore, finger rings are an appropriate locus for imbedding patient monitoring sensors and wireless transmitter in order to keep track of the patient twenty-four hours a day. Other articles of apparel may also be used in the manner described below with respect to finger rings.

Figure 1:
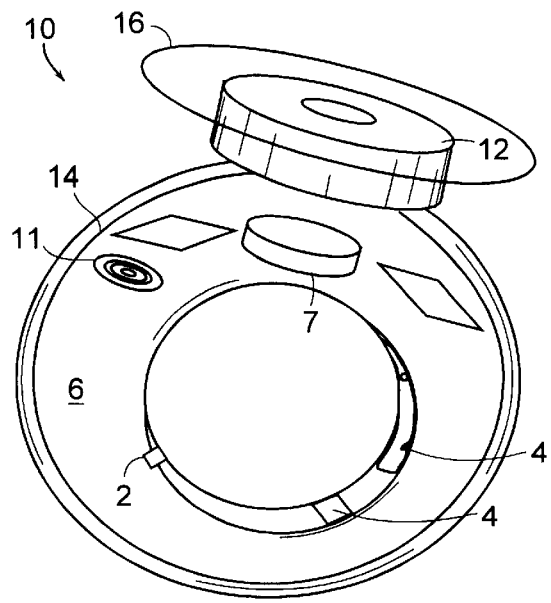
FIG. 1 is a perspective view of a finger ring sensor according to an embodiment of the invention.

A simple finger ring sensor with a wireless transmitter has been designed to demonstrate the concept. As shown in FIG. 1, one or more photo diodes 2 and one or more light-emitting diodes (LEDs) 4 are imbedded in a ring 10 facing each other inside the ring. The LEDs may emit light in the visible or infrared, and may be particularly chosen to emit light at one or more specified wavelengths, such as the isobestic wavelength discussed below. The pulse of the patient may be detected as a periodic change in the sensor output. This ring may be placed on one of the fingers. In a preferred embodiment, ring 10 is placed on the middle finger, which is not only convenient for wearing the ring but also suitable for counting pulse. The outer skin of the middle finger is thin, particularly at the sides of the finger, and a digital artery runs right beneath the thin skin. With an appropriate threshold, the sensor detecting the beat produces a pulse train of on-off signals and the pulse-train is sent to a transmitter (not shown) contained within an electronics module 6 which, in a preferred embodiment, is realized as a flexible printed circuit board.

When optical sensors are used, interference from the ambient light may corrupt the photo probe signals. As the patient moves, the ambient light coming to the ring photo probes varies, resulting in inconsistent data. A simple approach to preventing ambient light interference is to acquire the signal when all LEDs are turned off, and subtract this background effect from the measured signals. In accordance with an embodiment of the present invention, the optical sources, which may be LEDs, may be temporally modulated, and detection may be performed using synchronous detection techniques known to persons of ordinary skill in the art of signal processing.

Figure 2A:
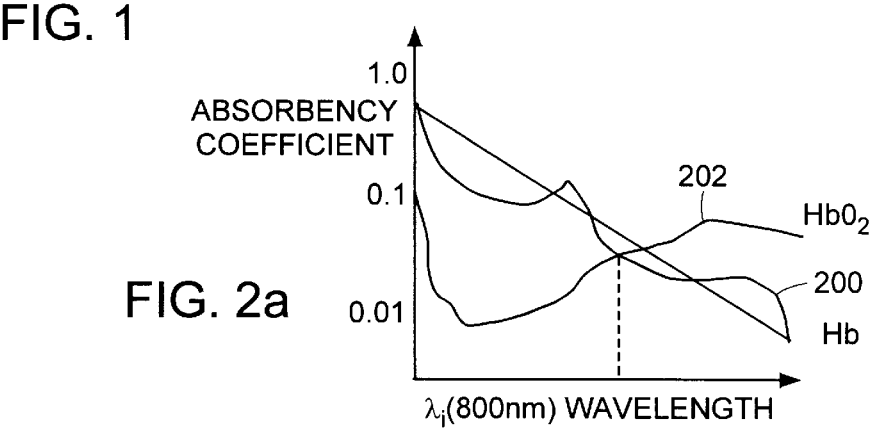
FIG. 2a depicts infrared spectra typical of hemoglobin and oxygenated hemoglobin, showing the isobestic wavelength employed in an embodiment of the present invention.
Figure 2B:
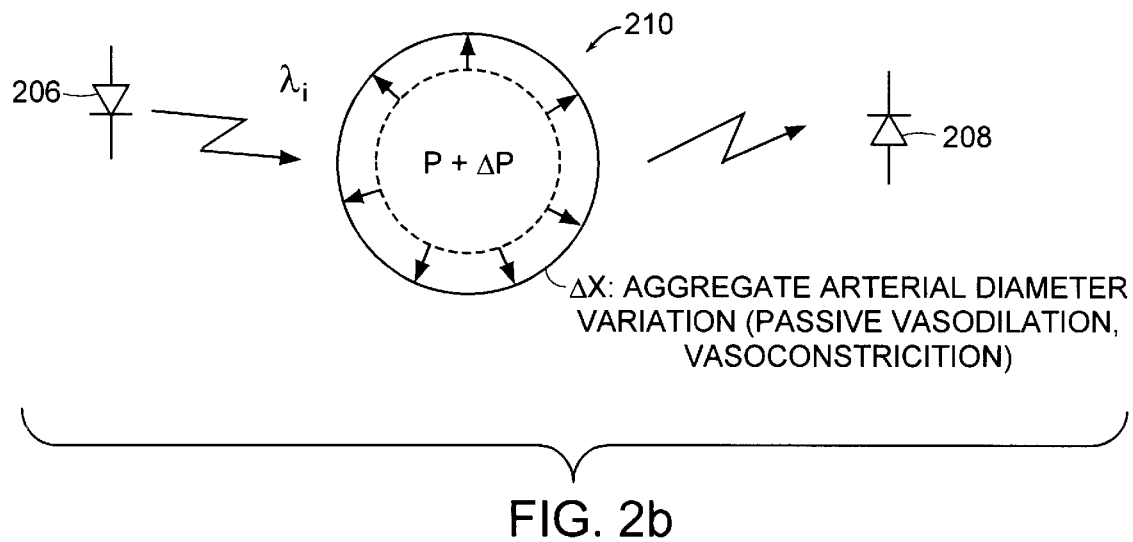
FIG. 2b is a schematic showing the measurement of arterial diameter variation in accordance with an embodiment of the present invention.

Referring now to FIG. 2a, arterial blood flow and pressure may be measured using LEDs emitting at the wavelength corresponding to the isobestic point of hemoglobin and oxygenated hemoglobin, at approximately 800 nanometers. The absorption coefficients of hemoglobin 200 and oxygenated hemoglobin 202 are plotted as a function of wavelength $\lambda$. At the isobestic wavelength $\lambda_i$, the optical absorption is insensitive to the fraction of oxygenated hemoglobin. Thus, as shown in FIG. 2b, the aggregate arterial diameter variation $\Delta x$ of artery 210 can be measured directly. Since arterial diameter, flow rate, and pressure are directly related, variation of the arterial diameter is proportional to changes $\Delta P$ in the arterial pulse pressure, so that the pulse may be measured with light emitted by LED 206 at the isobestic and detected by photo detector 208, without using a cuff.

Figure 3:
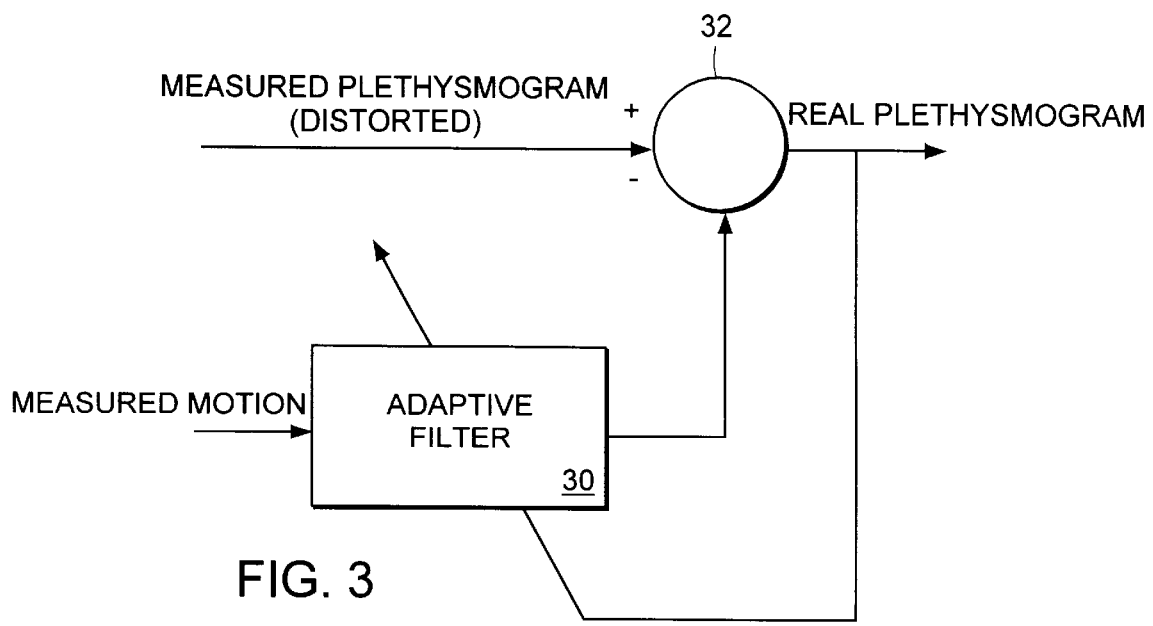
FIG. 3 is a schematic diagram of a motion filtering scheme in accordance with an embodiment of the present invention.

Referring, again, to FIG. 1, a major source of interference with sensor readings in wearable physiological sensors is that of artifacts induced in the signal train by motion of the patient. In accordance with a preferred alternate embodiment of the invention, motion artifacts are reduced or eliminated by using one or more accelerometers 7 to detect body motion and techniques of adaptive digital filtering known to persons skilled in the art of signal processing to eliminate motion artifacts in the signal train. The accelerometers may be any microelectromechanical systems (MEMS) accelerometer, as known to persons of ordinary skill in the art of instrumentation. As shown schematically in FIG. 3, in adaptive noise cancellation, adaptive filter 30, which, in a preferred embodiment is a digital filter, adaptively eliminates interference due to the motion artifact by removing, by means of summer 32, the motion signals from the sensor signals.

Referring again to FIG. 1, a transmitter 11 of the finger ring sensor transmits a wave which propagates without wires, such as a radio wave, an optical or infrared wave, or an ultrasound wave transmitted through the air. A radio transmitter is considered by way of example. In a preferred embodiment, radio transmitter 11 is a narrow-band, short-range, compact transmitter used for radio-controlled model cars, and transmission is via antenna coils 14 and 16, which, by virtue of their orthogonal polarizations, provide a radio signal which, in the far field, may be detected without sensitivity to a particular polarization. Various modulation schemes known to persons skilled in the art may be employed to encode information on the transmitted signal. These include, for example, amplitude, frequency, or pulse-code modulation. Power is provided by battery 12.

The temporal profile of the pulse pressure curve is dependent upon the compliance of the arterial wall and other parameters. In accordance with an embodiment of the invention, visco-elastic properties of the digital arteries may be derived by correlating the dynamic response of the plethysmographic signal to finger movements as measured by the MEMS accelerometer described above. This dynamic model of digital arteries may further be used to estimate the blood pressure and blood flow.

Figure 4:
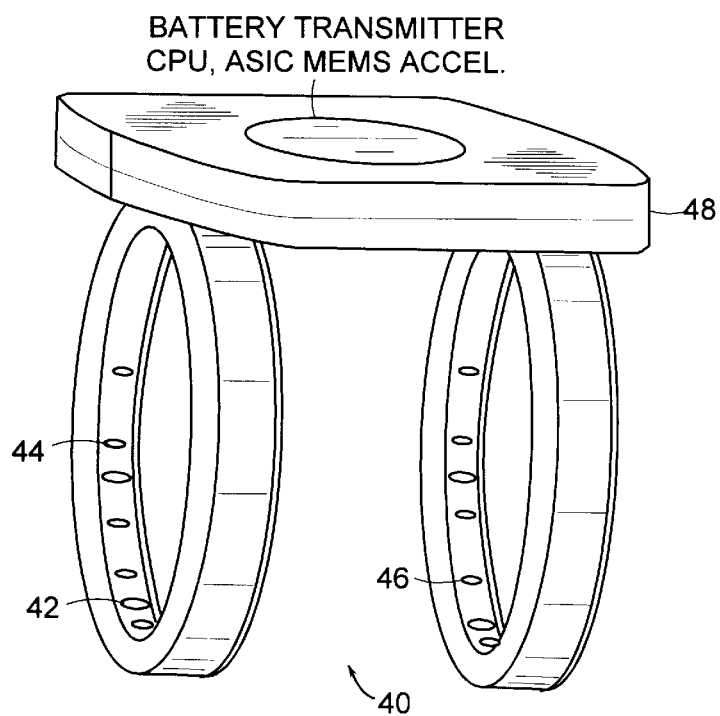
FIG. 4 is a perspective view of a dual ring finger sensor in accordance with an embodiment of the present invention.

Referring now to FIG. 4, in an alternate embodiment of the invention, spatially distributed optical sensors are employed in the ring configuration to monitor a patient's health conditions. Photo diodes 42 and LEDs 44 of appropriate wavelengths may be imbedded not only along the ring facing inwards, but also distributed in the longitudinal direction of the finger or other body member with a double-band configuration 40. The signal processing electronics, transmitter, antenna, battery, and MEMs accelerometer are contained within sensor module 48 in a manner described with reference to FIG. 1. Lights to be transmitted and reflected through the tissue of the body member may be collected three-dimensionally and integrated to estimate the patient's arterial blood pressure and blood flow, arterial blood volume, hematocrit, and oxygen saturation. Hematocrit refers to the volume percentage of erythrocytes in the patients blood. Similarly, other blood concentrations may be derived by suitable choice of optical wavelengths.

More particularly, sensors distributed longitudinally on separate bands may be used to acquire the pulse wave transit time by measuring the time difference of the plethysmographic pulse waves between two points along an artery since the pulse wave transit time is functionally related to the blood pressure.

In accordance with an additional embodiment of the invention, the absolute blood flow may be measured based on electrical impedance plethysmogram (EIP) by utilizing double-band ring sensors 40. Electrodes 46 attached at the two bands can provide measurement of the impedance change in a body segment, which is directly mediated by blood volume change. Then, an integration of the impedance change over time, together with a measurement of blood volume, may provide a direct determination of the influx of blood.

In an alternate embodiment of the invention, phase modulation spectroscopy (PMS) is used to detect, locate and characterize the optical properties of an heterogeneity such as arterial blood in human tissue. In PMS, the light intensity of the source is sinusoidally modulated and the phase shift is measured at a detector. The obtained phase shift is related to the mean pathlength of the detected photons, which in turn depends on the optical properties of the heterogeneity, and more accurate measurements may be made of blood pressure, blood flow and oxygen saturation and other physiological properties that cannot be measured non-invasively otherwise. The PMS technology along with the multiple photo detectors may also provide the relative position of the ring to the patient's finger, compensating for the uncertainty due to misalignment of the ring.

Figure 5:
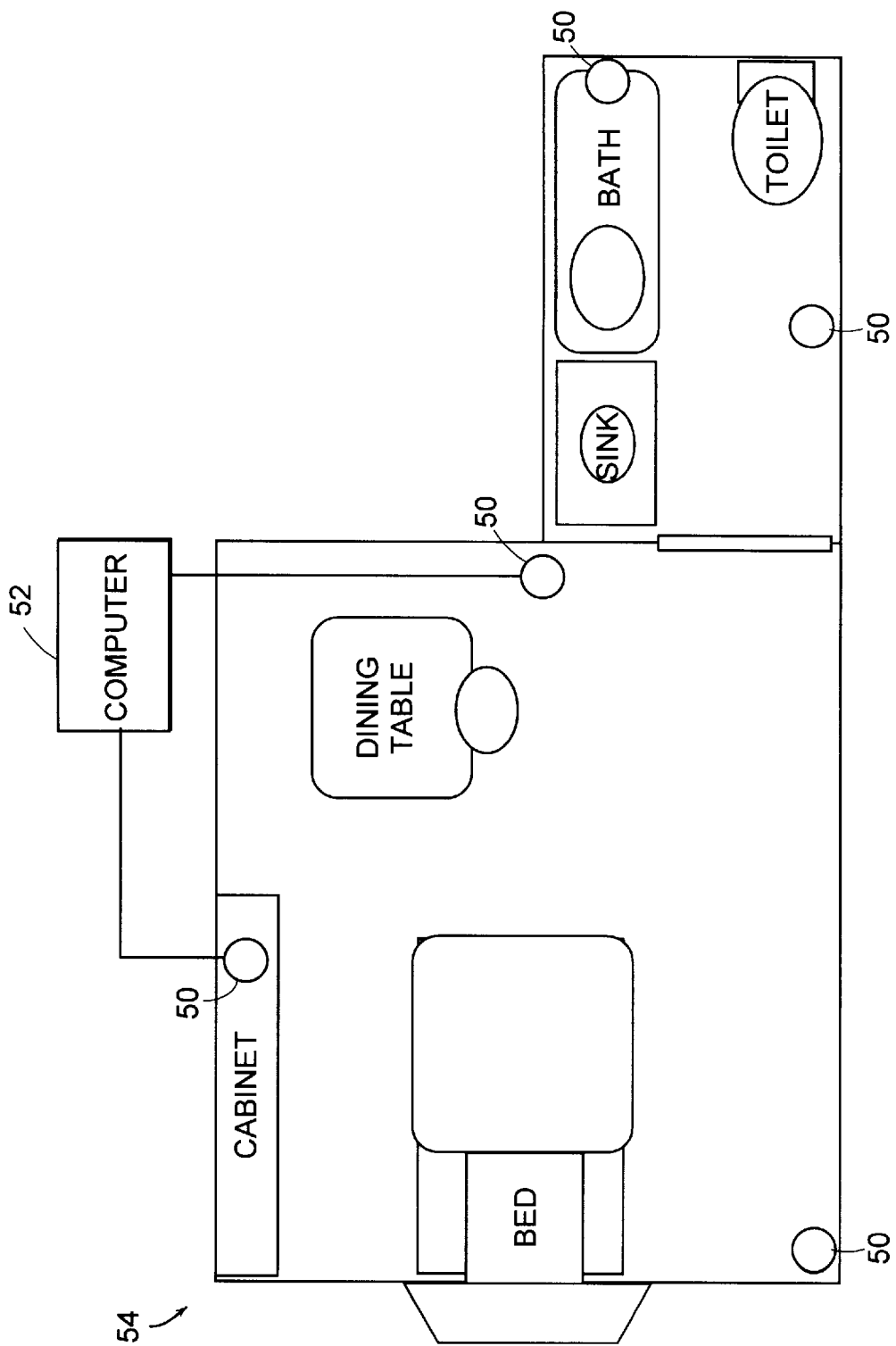
FIG. 5 is a diagram of a typical home layout showing receiver locations according to an embodiment of the present invention.

Referring now to FIG. 5, one or more stationary receivers 50 installed in the patient's home 54 detect this radio signal and provide it to a home computer 52. In a preferred embodiment of the invention, the pulse may be counted by home computer 52 rather than at the location of the sensor, and the home computer may decide, based on programmed criteria, whether a warning signal must be sent to a medical professional. In an alternate embodiment of the invention, preprocessing may be performed at the location of the sensor itself. In addition to measuring the pulse, other physiological parameters may be similarly monitored by the sensor and telemetered to a remote receiver. The use of tactile, electrical, thermocouple, and optical sensors, as well as other sensors for measuring such physiological parameters as skin temperature, blood flow, and blood constituent concentration are known in the art and are within the scope of the present invention.

The location of the ring wearer can be estimated by using known techniques of radio location sensing in conjunction with the transmitter described above. The objective of using many receivers 50 installed within a house is twofold:

to cover the entire house, so that no matter where the wearer moves within the house, the transmitted signal may be received;

to locate the ring wearer, using known methods of radio location sensing.

The accuracy of position estimation can be improved by considering the properties of radio signal propagation within the indoor environment. In general, the magnitude of received signal is inversely related to the distance from the transmitter. In an indoor environment, however, the signal propagates through multiple paths due to reflection and diffraction at the walls and edges, resulting in a complex, nonlinear distance-power relationship. However, the configuration of the house does not vary and the location of major furnishings does not change either for a long period of time. Therefore, the relationship between the location of the ring wearer and the magnitude of the received signal at each receiver installed in the house may be substantially constant over the period. By calibrating the transmitter-receiver relationship, a nonlinear map between the ring wearer's position and the receiver readings may be established. This allows the ring wearer's position to be estimated.

Figure 6:
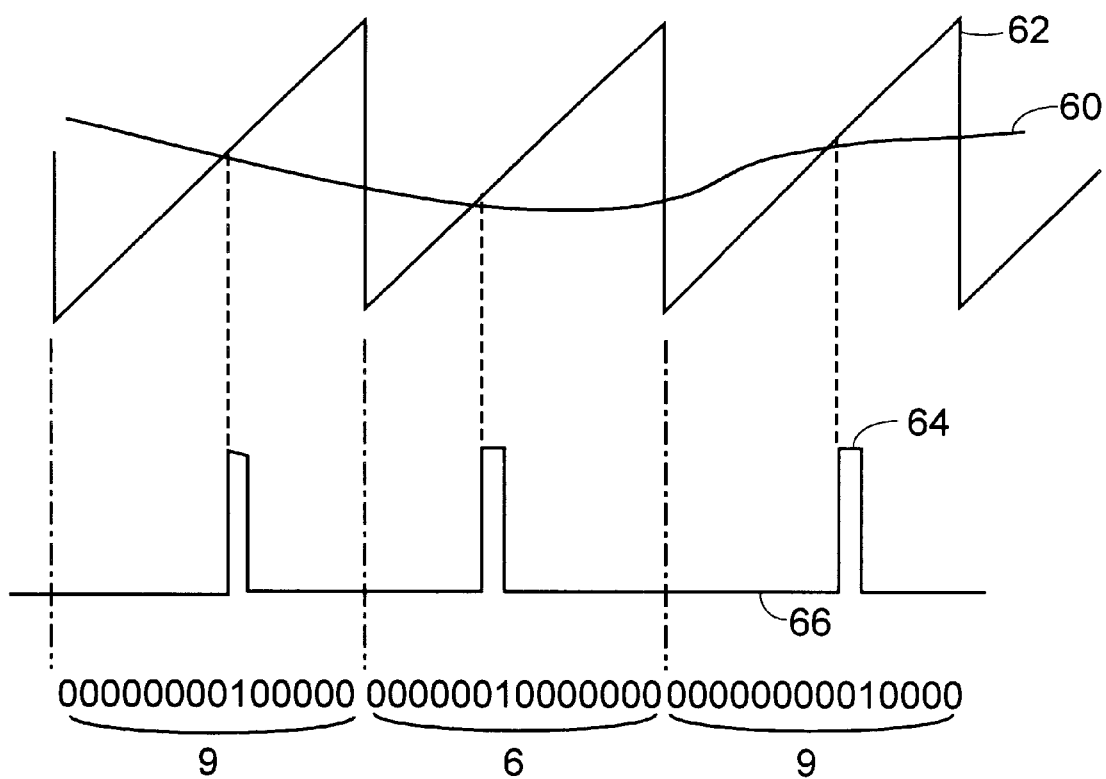
FIG. 6 depicts a unary encoding method in accordance with an embodiment of the present invention.

In order to reduce the power consumption of the patient monitor, a unary data transmission protocol may be employed in accordance with a preferred embodiment of the invention. Referring now to FIG. 6, this protocol is similarly applicable to other situations where power consumption is critical. The unary transmission protocol is preferably implemented by providing transmitter and receiver circuits such that the pulse width of 1-bit is minimized while assuring that every 1-bit can be correctly received by the receiver. At the software layer, a unary transmission protocol is employed that reduces the number of 1-bits while carrying the same amount of information.

In the standard RS-232 protocol, the average number of 1-bits involved in the transmission of 8-bit binary data is four. This can be significantly reduced by using a different coding method. Each 8-bit sample is, instead, encoded into a unique (but longer) codeword with a reduced number of 1-bits. Consider a simple example illustrating this basic idea.

For simplicity, it may be assume that each physiological sample is encoded as a 4-bit binary number, which represents $2^4$=16 levels (from 0 to 15). A unary encoding of each sample will then consist of 16 bits, with each codeword consisting of only one 1-bit.

Thus, more particularly, the binary number 0111 (which represents level 7), for example, becomes, in unary encoding, 0000000010000000. Similarly, the binary number 1111 (which represents level 15) in unary encoding is 1000000000000000.

Any datum, such as the value 60 of a variable plotted as a function of time 66 that can be assigned a numerical value may be encoded in the manner described. The assignment scheme depicted in FIG. 6, where a pulse 64 is triggered by signal 60 crossing sawtooth 62 imposes certain sampling requirements relative to the time rate of change of the signal. Other sampling schemes are also within the scope of the claimed invention. In general, a k-bit binary-encoded sample can be uniquely transformed into a 2k-bit unary-encoded sample, transmitted at a specified increment of time after a fiducial time to provide synchrony of transmission and detection. The reduction in power consumption using this unary encoding scheme is determined as follows: For k=8, each binary-encoded sample will have four 1-bits on average, whereas each unary-encoded sample requires exactly one 1-bit. This results in a factor of 4 in power reduction for k=8. It is easy to see that we will save a factor of k/2 in power consumption using unary encoding for general k-bit binary-encoded samples. Since the encoding scheme transforms each 8-bit sample to a longer codeword, a higher bit rate may be provided in order to obtain the same rate of data transmission.

The methods described herein may have applications besides the clinical and home healthcare applications in terms of which the invention has been described. Generally, the invention may be applied in air conditioning control, home appliances, automobiles, and security, as well. The described embodiments of the invention are intended to be merely exemplary and numerous variations and modifications will be apparent to those skilled in the art. All such variations and modifications are intended to be within the scope of the present invention as defined in the appended claims.

We claim:

1. A monitoring system for monitoring the health status of a patient, comprising:
   a. a finger ring to be worn by the patient, the finger ring comprising:
      i. at least one sensor for providing a signal based on at least one of skin temperature, blood flow, blood constituent concentration, and pulse rate of the patient;
      ii. a transmitter for converting the signal to a wave; and
      iii an accelerometer disposed within the finger ring for removing signal artifacts due to finger motion;
   b. at least one receiver for receiving the wave from the finger ring; and
   c. a controller for analyzing the wave and determining an abnormal health status.

2. A monitoring system according to claim 1, wherein the controller further includes a means for determining the location of the patient.

3. A monitoring system according to claim 1, wherein the wave is a radio wave.

4. A monitoring system according to claim 1, wherein the wave is a light wave.

5. A monitoring system according to claim 1, wherein the wave is an ultrasound wave.

6. A monitoring system according to claim 1, wherein the sensor includes a temperature sensor for measuring skin temperature.

7. A monitoring system according to claim 1, wherein the sensor includes an optical sensor for measuring at least one of the blood flow, blood constituent concentration, and pulse rate of the patient.

8. A monitoring system according to claim 7, wherein the optical sensor comprises a modulated source and synchronous detector.

9. A monitoring system according to claim 7, wherein the sensor comprises an optical source and an optical detector.

10. A monitoring system according to claim 9, wherein the optical source has a wavelength substantially corresponding to the isobestic point of hemoglobin and oxygenated hemoglobin.

11. A monitoring system according to claim 9, wherein the optical source is a light emitting diode.

12. A monitoring system according to claim 7, wherein the optical sensor comprises a plurality of optical sources employing temporal and spatial modulation.

13. A monitoring system according to claim 1, wherein the at least one sensor is an electrical impedance plethysmograph.

14. A monitoring system for monitoring the health status of a patient, comprising:
   a. a monitor having a first and a second band to be worn by the patient on a single finger, the monitor comprising:
      i. at least one sensor disposed on the first band for providing a first signal based on at least one of skin temperature, blood flow, blood constituent concentration, and pulse rate of the patient;
      ii. at least one sensor disposed on the second band for providing a second signal based on at least one of skin temperature, blood flow, blood constituent concentration, and pulse rate of the patient; and
   b. a controller for analyzing the first and second signals and determining a physiological characteristic of the patient.

15. A monitoring system according to claim 14, wherein the physiological characteristic is one of the group of arterial blood flow, hematocrit, and blood oxygen saturation.

16. A monitoring system according to claim 14, further comprising:
   a. a transmitter for converting the first and second signals to a wave; and
   b. at least one receiver for receiving the wave from the monitor.

* * * * *